: | United States Patent [19] | [11] 4,225,709 |
| --- | --- |
| Hegar et al. | [45] Sep. 30, 1980 |

[54] PRODUCTION OF 2,4-DIFLUORO-6-AMINO-S-TRIAZINE

[75] Inventors: Gert Hegar, Schönenbuch; Henri Riat, Arlesheim, both of Switzerland

[73] Assignee: Ciba-Geigy, AG, Basel, Switzerland

[21] Appl. No.: 1,574

[22] Filed: Jan. 8, 1979

[30] Foreign Application Priority Data

Jan. 18, 1978 [CH] Switzerland .......................... 516/78

[51] Int. Cl.$^2$ .......................................... C07D 251/44
[52] U.S. Cl. ................................................ 544/194
[58] Field of Search ........................................ 544/194

[56] References Cited

U.S. PATENT DOCUMENTS 3,576,804  4/1971  Klauke et al. ..................... 260/248

FOREIGN PATENT DOCUMENTS 1076696  3/1960  Fed. Rep. of Germany.

OTHER PUBLICATIONS

O. P. Shkurko et al., *Zh. Org. Khim.*, vol. 9, No. 5, pp. 1012–1014, (1973).
Roesky et al., *Chem. Ber.*, vol. 102, pp. 2330–2335, (1969).

*Primary Examiner*—John M. Ford
*Attorney, Agent, or Firm*—Prabodh I. Almaula

[57] ABSTRACT

The invention provides a process for the production of 2,4-difluoro-6-amino-s-triazine, which comprises reacting cyanuric fluoride in aqueous solution with ammonia or an ammonium salt, at a temperature between −5° C. and +10° C. and a pH value between 7.25 and 9.

5 Claims, No Drawings

PRODUCTION OF 2,4-DIFLUORO-6-AMINO-S-TRIAZINE

Hitherto, 2,4-difluoro-6-amino-s-triazine of the formula

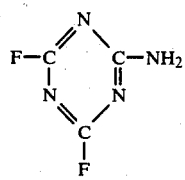

has only been obtainable by reacting 2,4,6-trifluoro-s-triazine (cyanuric fluoride) with ammonia in an anhydrous medium, for example ether, at −5° to −10° C. [O. P. Shkurko et al., Zh. Org. Khim 9 (5) 1012–4, (1973)].

It has now been found that 2,4-difluoro-6-amino-s-triazine can also be obtained by reacting cyanuric fluoride with ammonia in aqueous solution and carrying out the reaction at low temperature and in a neutral to weakly alkaline pH range. Instead of using ammonia, it is also possible to use an ammonium salt. Low temperature means in this case a temperature between −5° and +10° C. A neutral to weakly alkaline pH range means pH values between 7.25 and 9. The optimum pH range for the reaction of a cyanuric halide and ammonia is ordinarily 1 to 2 pH units lower than the $pK_s$ value of the corresponding acid of the base employed. As the $pK_s$ value of the ammonium ion is 9.25 (G. Hagg, Die theoretischen Grundlagen der analytischen Chemie, Verlag Birkhäuser, Basel, 1950, page 48), it follows that the optimum pH range for the reaction of cyanuric fluoride with ammonia is between 7.25 and 8.5.

To obtain pure monocondensation product, it is essential to carry out the reaction at pH values within the indicated limits, for a large amount of discondensation product is formed above pH 9 and the hydrolysis of cyanuric fluoride predominates below pH 7.25.

Accordingly, the present invention provides a process for the production of 2,4-difluoro-6-amino-s-triazine, which comprises reacting cyanuric fluoride, in aqueous solution, with ammonia or an ammonium salt, at a temperature between −5° and +10° C. and a pH value between 7.25 and 9. Preferably, the reaction is carried out at a pH value between 7.25 and 8.5.

A preferred embodiment of the invention consists in carrying out the reaction continuously. This is accomplished by adding the reactants, cyanuric fluoride and ammonia, continuously. The procedure can be as follows:

1. The reactor is charged with a small amount of ammonia in aqueous solution and then cyanuric fluoride and ammonia are added continuously in the molar ratio of about 1:2. The small excess of ammonia present in the solution acts as acid acceptor in the reaction.

2. The reactor is charged with an aqueous solution of an ammonium salt to which cyanuric fluoride is added continuously, while simultaneously liberating a corresponding amount of ammonia from the ammonium salt by continuous addition of an alkali metal hydroxide.

Instead of using an alkali metal hydroxide, it is also possible to use an alkali metal carbonate or bicarbonate or, if desired, also an alkaline earth metal hydroxide or carbonate.

Suitable ammonium salts are for example: ammonium chloride, ammonium sulfate and ammonium nitrate.

Because of the necessity to maintain the indicated pH values, and because of the rapid hydrolysis of cyanuric fluoride in water, it is not advantageous to charge the reaction vessel with cyanuric fluoride and to add ammonia or an ammonium salt and alkali.

The process of the present invention is surprising, for it was not to be expected that, in spite of the high basicity and pronounced nucleophilic properties of the ammonia employed, and in spite of the high reactivity of the fluorine atoms at the s-triazine ring, the monosubstitution product could be obtained successfully from aqueous solution in good yield.

The 2,4-difluoro-6-amino-s-triazine is a valuable intermediate which is suitable, in particular, for the manufacture of dyes. Thus reaction of 2,4-difluoro-6-amino-s-triazine with water-soluble dyes which contain amino groups yields valuable reactive dyes which are distinguished by high reactivity and good fastness properties of the dyeings obtained therewith. 2,4-Difluoro-6-amino-s-triazine can also be used for the manufacture of textile finishing agents, fluorescent whitening agents, photochemicals, crosslinking agents, pesticides and pharmaceutical preparations.

The invention is illustrated by the following Examples, in which the parts are by weight.

EXAMPLE 1

66 parts of cyanuric fluoride are added dropwise in the course of 60 minutes to an ice-cold solution of 27.5 parts of ammonium chloride in 500 parts of water, while keeping the pH between 7.8 and 8.5 by the simultaneous addition of 5 N sodium hydroxide solution and the temperature of 0°–2° C. by the addition of ice. The 2,4-difluoro-6-amino-s-triazine precipitates in the form of a white crystalline substance, which is collected by filtration and dried over calcium chloride in vacuo. Yield: 42.5 parts (65% of theory).

The substance is readily soluble in acetone. In water, hydrolysis occurs. The substance has no true melting point and decomposes strongly on being heated.

Analysis: $C_3H_2N_4F_2$, calculated N 42.43% F 28.77% found N 42.5% F 28.5%.

2,4-Difluoro-6-aminotriazine is obtained in analogous manner by using 42 parts of ammonium nitrate or 35 parts of ammonium sulfate instead of ammonium chloride.

EXAMPLE 2

To a mixture of 150 parts of water and 100 parts of ice are added 5 parts of a 24% aqueous ammonia solution. With good stirring, 33 parts of cyanuric fluoride are then introduced continuously in the course of 5 minutes. The pH of the reaction mixture is kept at 7.7 to 8 by the further dropwise addition of 24% ammonia solution. When the addition of cyanurci fluoride is complete, stirring is continued for 10 minutes at pH 8. The crystalline precipitate is then filtered with suction, washed well with ice-water to remove hydrolysis products of cyanuric fluoride, and dried. Yield: 23 parts of 2,4-difluoro-6-amino-1,3,5-triazine.

EXAMPLE 3

The procedure of Example 2 is repeated, except that 50 parts of ammonium chloride instead of ammonia are added to the aqueous solution before the addition of cyanuric fluoride is begun. Yield: 25 parts of 2,4- difluoro-6-amino-1,3,5-triazine (77% of theory, based on the cyanuric fluoride employed) after completion of the reaction and working up in analogous manner.

EXAMPLE 4

64 parts of the copper complex of N-(2-carboxy-5-sulfophenyl)-N'-(2'-hydroxy-3'-amino-5'-sulfophenyl)-ms-phenylformazane (disodium salt) are dissolved in 400 parts by volume of water at room temperature. Then 13.2 parts of freshly prepared 2-amino-4,6-difluoro-1,3,5-triazine are added and the mixture is stirred at room temperature, while keeping the pH at 7 to 7.5 by the simultaneous addition of sodium hydroxide solution. As soon as no more starting material can be detected in the reaction mixture, the reactive dye of the formula

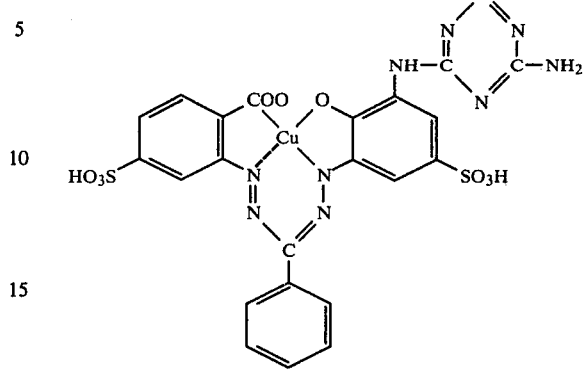

is precipitated by addition of sodium chloride, collected by filtration and dried. It dyes cotton in fast blue shades employing the conventional methods for dyeing with reactive dyes.

What is claimed is:
1. A process for the production of 2,4-difluoro-6-amino-s-triazine, which comprises reacting cyanuric fluoride, in aqueous solution, with ammonia or an ammonium salt, at a temperature between $-5°$ and $+10°$ C. and a pH value between 7.25 and 9.
2. A process according to claim 1, wherein the reaction is carried out at a pH value between 7.25 and 8.5.
3. A process according to either of claims 1 or 2, wherein the reaction is carried out continuously.
4. A process according to claim 3, wherein cyanuric fluoride and ammonia are added continuously in a molar ratio of about 1:2 to a weakly ammoniacal aqueous solution.
5. A process according to claim 3, wherein cyanuric fluoride is added continuously to the aqueous solution of an ammonium salt and a corresponding-amount of ammonia is simultaneously liberated from the ammonium salt by the continuous addition of an alkali metal hydroxide.

* * * * *